United States Patent [19]

Polito et al.

[11] 4,347,059
[45] * Aug. 31, 1982

[54] $T_3$ UPTAKE POLARIZATION FLUOROIMMUNOASSAY

[75] Inventors: Alan J. Polito, Irvine; Kurtis R. Bray, Garden Grove, both of Calif.

[73] Assignee: Beckman Instruments, Inc., Fullerton, Calif.

[*] Notice: The portion of the term of this patent subsequent to Aug. 31, 1999, has been disclaimed.

[21] Appl. No.: 187,239

[22] Filed: Sep. 15, 1980

[51] Int. Cl.³ .................... G01N 33/52; G01N 33/54; G01N 33/78

[52] U.S. Cl. .................... 23/230 B; 23/923; 424/1.5; 435/7; 435/8

[58] Field of Search .................... 435/7, 8; 23/230 B; 424/1, 1.5, 8

[56] References Cited

U.S. PATENT DOCUMENTS 3,961,894 6/1976 Gordon et al. .................... 424/1.5
4,158,703 6/1979 Polito .................... 424/1
4,272,505 6/1981 Smith .................... 23/230 B

OTHER PUBLICATIONS

Murphy, B. E. P., et al., *J. Clin. Endocrinol.*, 24:187 (1964).
Chopra, I. J., *J. Clin. Endocrinol.*, 34:938 (1972).
Osorio, C., et al., *Clin. Sci.*, 21:355 (1961).
Hamolsky et al., *J. Clin. Endocrinol*, 17:33 (1957).
Dandliker, W. D. et al., *Immunochem.*, 7:799 (1970).
Dandliker, W. D., et al., *Research Communications & Chemical Pathology & Pharmacology*, 18 (1):147 (1977).
Levison, J. A., *Endocrinology*, 99:1129 (1976).
Dandliker, W. D., et al., *Immunochemistry*, 1:165 (1964).
Smith, D. S., *Fubs Letters*, 77 (1):25 (1977).
Ullman, E. F., et al., *J. of Biol. Chem.*, 251:4172 (1976).
Aalberse, R. C., *Clin. Chem. Acta*, 48:109 (1973).
Watson, R. A. A., et al., *Clin. Chem. Acta*, 73:51 (1976).
McGregor, A. R., et al., *Clin. Chim. Acta*, 83:161 (1978).

*Primary Examiner*—Michael S. Marcus
*Attorney, Agent, or Firm*—R. J. Steinmeyer; J. E. Vanderburgh; Robert S. Frieman

[57] ABSTRACT

A $T_3$ uptake polarization fluoroimmunoassay where a sample is assayed by contacting a serum sample with $T_3$ to form a solution, contacting the solution with a separating agent and incubating the same, separating $T_3$ bound to the separating agent from the serum sample, contacting the $T_3$ bound to the separating agent with an antibody against $T_3$, incubating and separating the agent-anti-body combination, separating free anti-body and contacting the free antibody with fluorescent labeled $T_3$ and fluorometrically measuring the fluorescence polarization.

11 Claims, 1 Drawing Figure

$T_3$ UPTAKE POLARIZATION FLUOROIMMUNOASSAY

BACKGROUND OF THE INVENTION

1. Field of the Invention

This invention relates to a $T_3$ uptake immunoassay and, in particular, to a $T_3$ uptake polarization fluoroimmunoassay.

2. Description of the Prior Art

As early as 1939, Treverrow (1) reported that hormonal iodine compounds such as thyroxine ($T_4$) constitute the major portion of the total serum iodine. Furthermore, these iodinated organic compounds could be distinguished from serum inorganic iodide because they are bound to serum protein. Since iodine constitutes 65 percent by weight of the $T_4$ molecule, serum protein-bound iodine (PBI) was employed as an index of serum $T_4$. This indirect measurement of serum $T_4$ was believed to be a good indicator of the thyrometabolic status of an individual (2,3,4). The normal range of PBI values was found to be 4–8 ug/100 ml; values below 4 ug/100 ml were consistent with hypothyroidism whereas values above 8 ug/100 ml were indicative of thyrotoxicosis (hyperthyroidism).

A major pitfall of the PBI test is its inherent lack of specificity since high levels of inorganic iodide, radioopaque dyes and certain drugs give abnormally high values. In 1964, Murphy et al. (5) introduced their competitive protein binding analysis (CPB) for serum $T_4$ which solved most of the nonspecificity problems associated with the PBI test. Due to the fact that CPB tests for serum $T_4$ also required an extraction of the $T_4$ from the remainder of the serum components, recovery variability has lead to problems both in accuracy and precision.

Recently, radioimmunoassay (RIA) has become the method of choice for measuring serum $T_4$ (6). The RIA technique can be run directly on serum without extraction and therefore yields a simple and yet highly specific test. In general, results from RIA are from 5 to 25 percent higher than those from CPB tests.

Although the direct measurement of serum $T_4$ is not influenced by exogenous iodine, the value obtained will be influenced by the level of the circulating $T_4$ binding proteins. A number of states which are totally unrelated to thyroid disease may cause abnormal serum levels of $T_4$. Changes in the serum level of circulating $T_4$ binding proteins may cause the serum $T_4$ level to be high or low even in the presence of normal thyroid function. Although the primary protein involved is thyroxine binding globulin (TBG), both thyroxine binding prealbumin (TBPA) and albumin also bind $T_4$. Normally $T_4$ is distributed as follows: 65% on TBG, 25% on TBPA, and 10% on albumin (7). In general, changes in TBG concentrations correlate much better with anomalies in thyroid function tests, such as the PBI or total $T_4$ than do changes in TBPA (8).

Although the most accurate method to measure TBG concentrations involves the electrophoretic method of Orsorio et al. (9), the technique is too cumbersome for routine use. The method of choice which has been used for this purpose is one of the many variations of the triiodothyronine ($T_3$) uptake test. Hamolsky et al. (10) first performed this type of test. All $T_3$ uptake tests are designed to assess the unsaturated binding capacity of serum proteins most notably TBG. The test is based on the fact that TBG binds $T_3$ less firmly than $T_4$ and therefore should not upset the equilibrium set-up between $T_4$ and TBG and, further, $T_3$ is not normally bound to TBPA.

In the $T_3$ uptake test an equilibrium is developed between the patient's serum, added labeled $T_3$ and an inert exogenous binder (separating agent) of the labeled $T_3$. One must add a sufficient amount of labeled $T_3$ to saturate the binding sites on the TBG after which the labeled $T_3$ that is unbound is adsorbed by the separating agent and the separating agent bound labeled $T_3$ is counted. Therefore, when the endogenous $T_4$ level is increased, as in hyperthyroidism, serum TBG is relatively saturated and the $T_3$ uptake will be high. Conversely in the hypothyroid state where $T_4$ output is low, the labeled exogenous $T_3$ will bind to the relatively unsaturated TBG yielding a low $T_3$ uptake.

Presently, radioassay is a method of choice for performing a $T_3$ uptake test. However, this $T_3$ uptake test has severe disadvantages in that radiolabeled $T_3$, e.g., $^{125}$I-labeled $T_3$, is relatively unstable and radioassay kits are restricted by regulations such as those governing the transport, handling, and storage of radioactive materials.

It would therefore be very desirable to develop an alternative $T_3$ uptake test which retains the advantages present in the radioassay technique but which overcomes the two problems inherent therein, namely the relative instability of radiolabeled $T_3$ and the restrictions placed upon radioassay kits.

Although the bases for various fluoroimmunoassays (11) such as fluorescent polarization (12–15), enhancement fluoroimmunoassay (16), fluorescent excitation transfer immunoassays (17), and fluorescent immunuabsorbent tests (18) have been described and demonstrated, to data, other than a fluorescent polarization assay of gentamicin (19) and dilantin (20) none of the above methodologies have been applied in a practical assay of proven clinical utility. For example, in the case of enhancement fluoroimmunoassays (16), it is reported that the variable levels of intrinsic serum fluorescence present an obstacle to the assay of patient samples.

Bibliography

1. Trevorrow, V., *J. Biol. Chem.*, 127:737 (1939).
2. De Mowbray, R. R., et al., *Lancet*, 2:511 (1952).
3. Sunderman, F. W., et al., *Amer. J. Clin. Path.*, 24:885 (1954).
4. Dailey, M. E., et al., *New Engl. J. Med.*, 254 (19):907 (1956).
5. Murphy, B. E. P., et al., *J. Clin. Endocrinol.*, 24:187 (1964).
6. Chopra, I. J., *J. Clin. Endocrinol.*, 34:938 (1972).
7. Robbins, J., et al.: Hormones in Blood, Gray, C. H., et al., eds., Academic Press, London, 2nd Ed., 1:430 and 447 (1967).
8. Thomas, J. A., et al.: Hormone Assays and Their Clinical Application, Loraine, J. A., et al., eds., Churchill Livingston, New York, 4th Ed., Vh. 12 (1976).
9. Osorio, C., et al., *Clin. Sci.*, 21:355 (1961).
10. Hamolsky et al., *J. Clin. Endocrinol.*, 17:33 (1957).
11. O'Donnell, *Analytical Chemistry*, 50 (5):189R (1978).
12. Dandliker, W. D. et al., *Immunochem.*, 7:799 (1970).
13. Dandliker, W. D., et al., *Research Communications and Chemical Pathology and Pharmacology*, 18 (1):147 (1977).

14. Levinson, J. A., *Endocrinology*, 99:1129 (1976).
15. Dandliker, W. D., et al., *Immunochemistry*, 1:165 (1964).
16. Smith, D. S., *Febs Letters*, 77 (1):25 (1977).
17. Ullman, E. F., et al., *J. of Biol. Chem.*, 251:4172 (1976).
18. Aalberse, R. C., *Clin. Chem. Acta*, 48:109 (1973).
19. Watson, R. A. A., et al., *Clin. Chem. Acta*, 73:51 (1976).
20. McGregor, A. R., et al., *Clin. Chim. Acta*, 83:161 (1978).

SUMMARY OF THE INVENTION

In accordance with the present invention an improved $T_3$ uptake test is provided which retains the advantages present in the radioassay technique but which overcomes the two problems inherent therein. The $T_3$ uptake test of the instant invention is a $T_3$ uptake polarization fluoroimmunoassay. More particularly, the protocol of the $T_3$ uptake fluoroimmunoassay of this invention comprises:

(a) contacting a sample to be assayed with $T_3$ to thereby form a solution;

(b) contacting an aliquot of the solution with a separating agent;

(c) incubating the aliquot-separating agent combination;

(d) separating $T_3$ bound to separating agent from serum bound $T_3$;

(e) contacting the $T_3$ bound to separating agent with an antibody against $T_3$, said antibody having a higher affinity for $T_3$ than the affinity of the separating agent for $T_3$;

(f) incubating the separating agent-antibody combination;

(g) separating free antibody and $T_3$ bound antibody from the separating agent;

(h) contacting the free antibody with fluorescent labeled $T_3$; and (i) fluorometrically measuring the fluorescent polarization in the mixture of step (h). The value obtained by the fluorometric measurement of step (i) is directly proportional to the serum uptake of the added $T_3$ and indirectly proportional to the conventional $T_3$ uptake value as measured via radioassay $T_3$ uptake methodologies.

DESCRIPTION OF THE PREFERRED EMBODIMENTS

Figure 1:
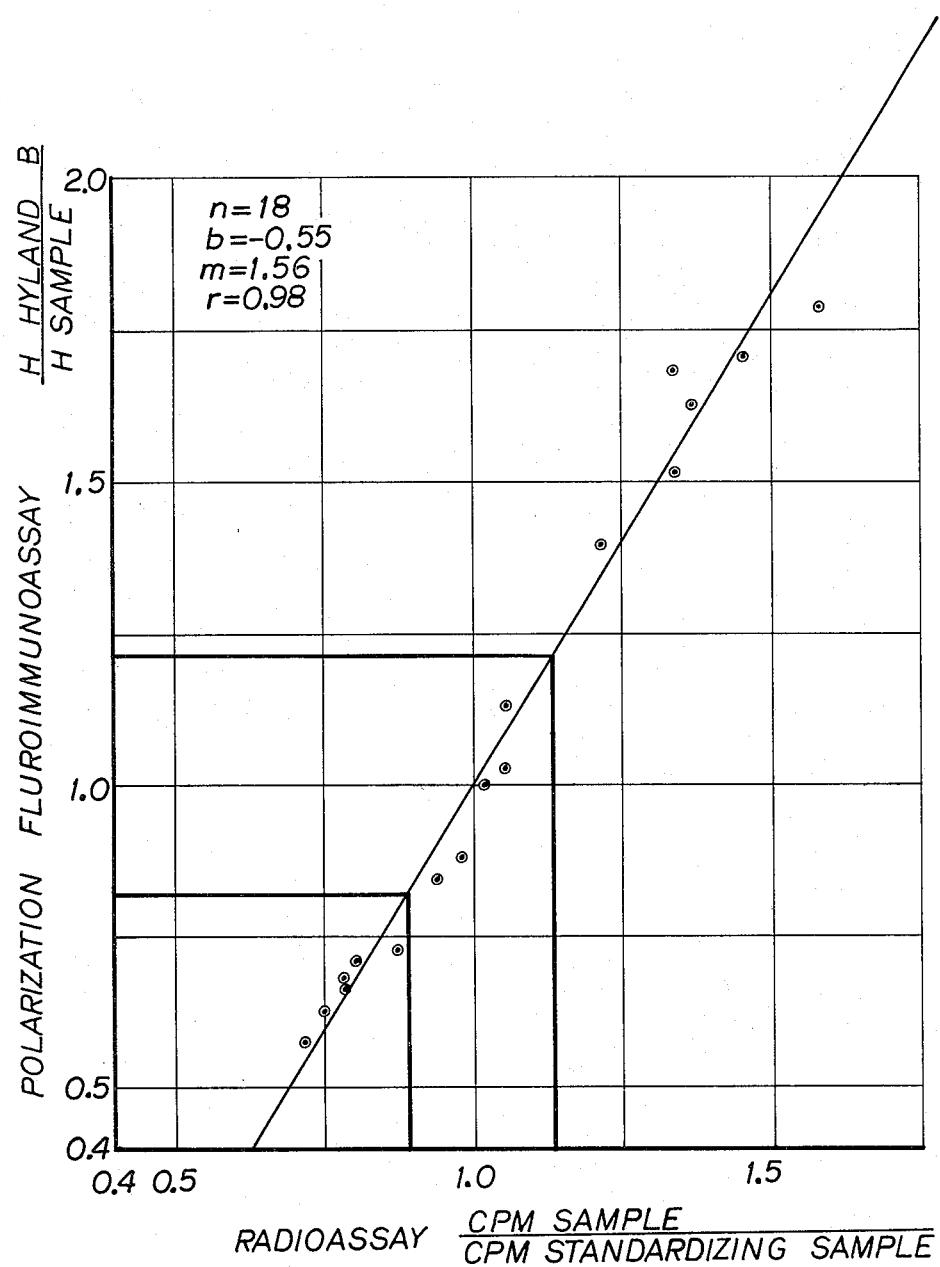
FIG. 1 is a correlation analysis of a radioassay $T_3$ uptake procedure versus a ratio of the peak rate of the control serum to the peak rate of the sample as obtained in a polarization fluoroimmunoassay uptake procedure within the scope of this invention.

Samples which can be assayed by the instant invention for $T_3$ uptake include biological fluids having either an unknown $T_3$ uptake (e.g., a patient's sample) or biological fluids having a known $T_3$ uptake (i.e., standards). Typical biological fluids include, but are not limited to, plasma and serum. Serum is the preferred biological fluid employed in the analysis of the instant invention.

Any separating agent whose affinity for $T_3$ is less than the affinity of serum proteins (most notably TBG) for $T_3$ can be used in the instant invention. Typical separating agents include, but are not limited to, bead-formed dextran gel and agarose. Preferably, the separating agent employed in the instant invention is bead-formed dextran gel.

Any antibody having a higher affinity for $T_3$ than the affinity of the particular separating agent for $T_3$ can be used in the instant invention. Typical $T_3$ antibodies include, but are not limited to, purified sheep, rabbit, and goat IgG fraction containing $T_3$ antibody.

Any suitable fluorescent label can be used to label the $T_3$. Fluorescent labels include, but are not limited to, fluorescien and rhodamine. Fluoroescien is the preferred fluorescent label.

The incubation time of step (c) is not critical and can be any convenient period of time. Preferably, this incubation step is conducted for about 5 to about 60 minutes, preferably for about 15 minutes.

Similarly, the incubation procedure of step (f) is not critical and can also be conducted for any convenient period of time. Preferably, this incubation step is conducted for about 0.5 to about 2 hours, and more preferably for about 1 hour.

The decrease in polarization fluorescence caused by contacting the free antibody with the fluorescent labeled $T_3$ can be measured by any well known fluorometric techniques via either an endpoint or kinetic methodology. Preferably, a kinetic fluorometric technique is employed in the assay of this invention.

Preferably, after step (g) the free antibody is contacted with a non-fluorescent surfactant. Non-fluorescent surfactants include, but are not limited to, octylphenoxy polyethoxy ethanol and polyoxyethylene sorbitan monolaurate. Octylphenoxy polyethoxy ethanol is the preferred non-fluorescent surfactant.

The problems of non-specific bonding and of variable background fluorescence caused by serum are overcome by step (d) of the procedure of the instant invention when the $T_3$ which is bound to the separating agent is removed from the serum.

The following examples are provided for the purposes of illustration only and are not intended to be limitations on the disclosed invention.

EXAMPLE 1

$T_3$ Uptake Polarization Fluoroimmunoassay

A. Reagents

1. Purified sheep IgG fraction containing $T_3$ antibody diluted 1/800 in B-2 buffer (0.075 M barbital buffer comprising, per liter of water, 15.6 gm sodium barbital, 2.0 gm sodium EDTA ((ethylenedinitrilo)tetraacetic acid), and 9.0 gm sodium chloride) containing 1 g/l gelatin.

2. Fluorescein labeled $T_3$ ($FT_3$) at a concentration of 250 pg $T_3$/50 $\mu$l in B-2 buffer containing 0.1 mg/ml insulin.

3. $T_3$ solution at a concentration of 2.5 ng/200 $\mu$l in B-2 buffer containing 1 mg/ml bovine serum albumin (BSA) and 1 mg/ml gelatin.

4. Octylphenoxy polyethoxy ethanol (0.01%) in B-2 buffer.

B. Preparation of Columns

1. Individual columns were prepared employing 5.0 ml aliquots obtained from a suspension of 25 gms of bead-formed dextran gel (sold under the trademark Sephadex G25 (Fine)) in about 500 ml of saline. Each column was fitted with a disc prepared from Whatman No. 2 brand filter paper and washed with 4.0 ml of B-2 buffer.

C. Sample Preparation

1. In clean borosilicate glass tubes 150 μl B-2 buffer, 50 μl sample, and 200 μl of $T_3$ solution were mixed. Next, 300 μl aliquots, of this mixture, were delivered on top of the individual columns, allowed to penetrate into the gel bed, and then incubated therein for about 15 minutes.

2. After 4.0 ml of B-2 buffer had been washed through each column, 300 μl of $T_3$ antibody was delivered on top of the individual columns and allowed to penetrate into the gel bed and then incubated therein for about 1 hour.

3. Finally, each column was washed with 1.5 ml of B-2 buffer and the eluants were collected in clean borosilicate tubes. Following the addition of 100 μl of B-2 buffer containing 0.01% octylphenoxy polyethoxy ethanol, the individual aliquots were vortexed.

D. Polarization fluoroimmunoassay of Free Antibody to $T_3$

1. Aliquots (500 μl) from each tube were reacted with fluorecein labeled $T_3$ and the resulting fluoroescein polarization of the aliquot was measured.

a. The data obtained are inversely related to the $T_3$ uptake of each sample. The data obtained from this experiment are set forth in Table I.

EXAMPLE 2

Radioassay $T_3$ Uptake

In order to evaluate the efficacy of the $T_3$ uptake polarization immunoassay of the instant invention, a correlation study was performed employing the following radioassay $T_3$ uptake procedure set forth in Tri-Tab $T_3$ Uptake Diagnostic Kit, Nuclear-Medical Laboratories, Inc., Dallas, Texas.

The data obtained via the above radioassay $T_3$ uptake protocol are set forth in Table I.

TABLE I

| Sample | Radioassay cpm Sample / cpm Standardizing Sample | Peak Rate (H) | Mean | Coeff. of Variation | Polarization Fluoroimmunoassay H Hyland B / H Sample |
|---|---|---|---|---|---|
| 1 | 0.68 | 879 / 902 / 840 | 890 | 1.83% | 0.58 |
| 2 | 0.70 | 819 / 811 | 830 | 1.79% | 0.62 |
| 3 | 0.76 | 823 / 806 | 817 | 1.04% | 0.63 |
| Hyland A | 0.76 | 776 / 764 | 791 | 2.68% | 0.65 |
| 4 | 0.77 | 799 / 757 | 782 | 3.17% | 0.66 |
| 5 | 0.85 | 744 / 601 | 750 | 1.22% | 0.69 |
| 6 | 0.93 | 632 / 580 | 616 | 3.56% | 0.84 |
| 7 | 0.98 | 600 / 524 | 590 | 2.40% | 0.88 |
| Hyland B | 1.01 | 510 / 519 | 517 | 1.91% | 1.00 |
| 8 | 1.05 | 482 / 448 | 500 | 5.23% | 1.03 |
| 9 | 1.07 | 447 / 381 | 448 | 0.16% | 1.15 |
| 10 | 1.20 | 369 / 304 | 375 | 2.26% | 1.38 |
| 11 | 1.30 | 314 / 340 | 309 | 2.29% | 1.67 |
| 12 | 1.32 | 343 / 304 | 342 | 0.62% | 1.52 |
| Hyland C | 1.35 | 324 / 317 | 314 | 4.50% | 1.65 |
| 13 | 1.35 | 326 / 306 | 322 | 1.98% | 1.65 |
| 14 | 1.42 | 305 / 296 | 306 | 0.23% | 1.69 |
| 15 | 1.58 | 300 | 298 | 0.95% | 1.74 |

FIG. 1 is a plot of the ratio of the counts per minute (cpm) for a sample being assayed to the cpm of the standardizing sample being assayed by a radioassay $T_3$ uptake procedure vs. the ratio of the peak rate for Hyland B to the peak rate for the sample being assayed by the instant invention. The plot shown in FIG. 1 demonstrates excellent correlation (r=0.98) between the assay of the instant invention and a conventional $T_3$ uptake radioassay. In addition, the average coefficient of variation for the data set forth in Table I is 2.01% which is comparable to the average coefficient of variation (2.33%) of the radioassay $T_3$ uptake procedure employed in Example 5.

Since the ratio of cpm Hyland B sample to cpm of the standardizing sample is 1.01 (see Table I), it can be concluded that the cpm for the Hyland B sample is substantially identical to the cpm of the standardizing sample employed in the radioassay $T_3$ uptake procedure.

As noted above, the value obtained by the fluorometric measurement of the instant invention is indirectly proportional to $T_3$ uptake values as measured via conventional radioassay $T_3$ uptake procedures. This relation can be mathematically shown as $$\frac{\text{Radioassay}}{\text{cpm standardizing sample}} \cdot \frac{\text{cpm sample}}{\text{cpm standardizing sample}} \alpha \frac{\text{Polarization Fluoroimmunoassay}}{\text{H sample}}$$

Since cpm Hyland B≃cpm standardizing sample, one can used Hyland B as the standardizing sample in the polarization fluoroimmunoassay under the assumption that cpm Hyland B is proportional to H Hyland B. Therefore, $$\frac{\text{cpm sample}}{\text{cpm standardizing sample}} \alpha \frac{H \text{ Hyland } B}{H \text{ sample}}$$

The fact that the assumption that cpm Hyland B is proportional to H Hyland B is correct is evidenced by the excellent correlation (r=0.98) between these two methodologies.

It should be noted that FIG. 1 graphically depicts the fact that the methodology of the instant invention yields a larger normal and hypothyroid region than obtainable with the radioassay $T_3$ uptake procedure employed in Example 5. This fact tends to make the methodology of the instant invention more accurate than that of the prior art.

Based upon this disclosure, many other modifications and ramifications will naturally suggest themselves to those skilled in the art. These are intended to be comprehended as within the scope of this invention.

The embodiments of the invention in which an exclusive property or privilege is claimed are defined as follows:

1. A $T_3$ uptake polarization fluoroimmunoassay procedure comprising:
   (a) contacting a serum sample to be assayed with $T_3$ to thereby form a solution, the amount of said $T_3$ being sufficient to assess the unsaturated binding capacity of serum proteins;
   (b) contacting an aliquot of said solution with a separating agent;
   (c) incubating said aliquot-separating agent combination;
   (d) separating $T_3$ bound to separating agent from said serum and thereby simultaneously removing non-specific serum effects as well as background fluorescence;
   (e) contacting said $T_3$ bound separating agent with an antibody against $T_3$, said antibody having a higher affinity for $T_3$ than the affinity of said separating agent for $T_3$ and the amount of said antibody being sufficient to remove at least substantially all of said $T_3$ from said separating agent;
   (f) incubating said separating agent-antibody combination;
   (g) separating free antibody and $T_3$ bound antibody from said separating agent;
   (h) contacting said free antibody with fluorescent labeled $T_3$; and
   (i) fluorometrically measuring the fluorescence polarization in said mixture of step (h);
   wherein said measurement is inversely proportional to the $T_3$ uptake of the sample being assayed.

2. The assay of claim 1 wherein said separating agent is selected from a group consisting of bead-formed dextran gel and agarose.

3. The assay of claim 1 wherein said fluorescent labeled $T_3$ is selected from a group consisting of fluorescein labeled $T_3$ and rhodamine labeled $T_3$.

4. The assay of claim 3 wherein after step (g) a non-fluorescent surfactant is contacted with said free antibody.

5. The assay of claim 4 wherein:
   (a) said separating agent is selected from a group consisting of bead-formed dextran gel and agarose;
   (b) said fluorescent labeled $T_3$ is selected from a group consisting of fluorescein labeled $T_3$ and rhodamine labeled $T_3$; and
   (c) after step (g) said free antibody is contacted with a non-fluorescent surfactant.

6. The assay of claim 5 wherein said separating agent is bead-formed dextran gel.

7. The assay of claim 5 wherein said fluorescent labeled $T_3$ is fluorescein labeled $T_3$.

8. The assay of claim 5 wherein said non-fluorescent surfactant is selected from a group consisting of oxylphenoxy polyethoxy ethanol and polyoxyethelene sorbitan monolaurate.

9. The assay of claim 5 wherein:
   (a) said separating agent is bead-formed dextran gel;
   (b) said fluorescent labeled $T_3$ is fluorescein labeled $T_3$; and
   (c) said non-fluorescent surfactant is selected from a group consisting of oxylphenoxy polyethoxy ethanol and polyoxyethelene soribatan monolaurate.

10. The assay of claim 9 wherein said non-fluorescent surfactant is octylphenoxy polyethoxy ethanol.

11. The assay of any one of claims 1–10 wherein said fluorometric measurement is a kinetic fluorometric measurement.

* * * * *